US005974155A

United States Patent [19]

Kashani et al.

[11] Patent Number: 5,974,155

[45] Date of Patent: Oct. 26, 1999

[54] SYSTEM AND METHOD FOR ACTIVELY DAMPING BOOM NOISE

[75] Inventors: Reza Kashani, Dayton, Ohio; David Naastad, Aurora, Colo.

[73] Assignee: The University of Dayton, Dayton, Ohio

[21] Appl. No.: 09/060,797

[22] Filed: Apr. 15, 1998

Related U.S. Application Data

[60] Provisional application No. 60/043,708, Apr. 15, 1997.

[51] Int. Cl.[6] .............................. A61F 11/06; H03B 29/00

[52] U.S. Cl. ...................... 381/71.14; 381/71.8; 381/71.4

[58] Field of Search ................................ 381/71.1, 71.4, 381/86, 71.8, 71.9, 94.1, 95, 71.14

[56] References Cited

U.S. PATENT DOCUMENTS

| | | |
|---|---|---|
| 4,689,821 | 8/1987 | Salikuddin et al. . |
| 4,876,722 | 10/1989 | Dekker et al. . |
| 5,125,241 | 6/1992 | Nakanishi et al. . |
| 5,310,137 | 5/1994 | Yoerkie, Jr. et al. . |
| 5,343,713 | 9/1994 | Okabe et al. . |
| 5,355,417 | 10/1994 | Burdisso et al. . |
| 5,373,922 | 12/1994 | Marra . |
| 5,394,478 | 2/1995 | Hathaway et al. . |
| 5,515,444 | 5/1996 | Burdisso et al. . |
| 5,558,298 | 9/1996 | Pla et al. . |
| 5,666,427 | 9/1997 | Kim ....................................... 381/71.1 |

FOREIGN PATENT DOCUMENTS

| | | |
|---|---|---|
| 0 081 594 A1 | 6/1983 | European Pat. Off. . |
| 2 284 282 | 5/1995 | United Kingdom . |
| WO 96/11466 | 4/1996 | WIPO . |

OTHER PUBLICATIONS

Article entitled "Modeling, Identification, and Feedback Control of Noise in an Acoustic Duct" from *IEEE Transactions on Control Systems Technology,* vol. 4, No. 3, May 1996.

"4:Inspec 1983–1997/EB W1, ©1997, Institution of Electrical Engineers, pp. 1–13".

"NASA—Recon Database Search Report. pp. 1–10".

"340:Claims (R)/US Patents ABS 1950—1996/Nov, ©1997 IFI/Plenum Data Corp. pp. 19–25".

"8:Ei; Compendex(R) 1970–1997/Mar WZ, ©1997, Engineering Info. Inc., pp. 14–18".

"Active damping of enclosed sound fields through direct rate feedback control" Robert L. Clark, J. Acoust. Soc. Am. 97(3), Mar. 1995, ©1995 Acoustical Society of America, pp. 1710–1716.

"Passive and Active Damping Augmentation Systems in the Fields of Structural Dynamics and Acoustics", R. Freymann, Structural Dynamics and Materials Conference–Mobile, Alabama Apr. 3–5, 1989, pp. 346–361.

*Primary Examiner*—Minsun Oh Harvey
*Attorney, Agent, or Firm*—Killworth, Gottman, Hagan & Schaeff, L.L.P.

[57] ABSTRACT

A system for actively damping low frequency noise in an enclosure is provided comprising an acoustic wave sensor, and acoustic wave actuator, and an electronic feedback loop. The acoustic wave actuator is substantially collocated with the acoustic wave sensor within an enclosure. The electronic feedback loop is operative to generate a signal at its output by applying a feedback loop transfer function. The feedback loop transfer function comprises a selected second order differential equation including a first variable representing a predetermined damping coefficient and a second variable representing a tuned natural frequency. The transfer function defines a frequency response having a characteristic maximum gain substantially corresponding to the value of the tuned natural frequency and creates a 90 degree phase lead substantially at the tuned natural frequency. The feedback loop output signal represents a rate of change of volume velocity to be produced by the acoustic wave actuator.

20 Claims, 7 Drawing Sheets

SYSTEM AND METHOD FOR ACTIVELY DAMPING BOOM NOISE

CROSS REFERENCE TO RELATED APPLICATIONS

This application claims the benefit of U.S. Provisional Application Ser. No. 60/043,708, ACTIVE BOOM NOISE CONTROL, filed Apr. 15, 1997.

BACKGROUND OF THE INVENTION

The present invention relates to a system and method for actively damping low frequency noise within an enclosure and, more particularly, to such a system and method wherein an electronic feedback loop is employed to drive an acoustic damping source within an enclosure such as an automobile cabin.

The principles of active noise control are well established and basically consist of detecting, by a microphone, the noise to be controlled, and replaying the detected noise in anti-phase via a loudspeaker so that the regenerated noise destructively interferes with the source noise. The following U.S. Patents, the disclosures of which are incorporated herein by reference, teach a variety of techniques for actively controlling noise within an enclosure: U.S. Pat. No. 5,558,298, issued to Pla et al. on Sep. 24, 1996; U.S. Pat. No. 5,535,283, issued to Susumu et al. on Jul. 9, 1996; U.S. Pat. No. 5,466,849, issued to Geisenberger on Nov. 14, 1995; U.S. Pat. No. 5,394,478, issued to Hathaway et al. on Feb. 28, 1995; U.S. Pat. No. 5,390,121, issued to Wolfe on Feb. 14, 1995; U.S. Pat. No. 5,355,417, issued to Burdisso et al. on Oct. 11, 1994; U.S. Pat. No. 5,343,713, issued to Okabe et al. on Sep. 6, 1994; U.S. Pat. No. 5,515,444, issued to Burdisso et al on May 7, 1996; U.S. Pat. No. 5,373,922, issued to Marra on Dec. 20, 1994; U.S. Pat. No. 5,310,137, issued to Yoerkie, Jr. et al. on May 10, 1994; U.S. Pat. No. 5,125,241, issued to Nakanishi et al. on Jun. 30, 1992; U.S. Pat. No. 4,689,821, issued to Salikuddin et al. on Aug. 25, 1987; and U.S. Pat. No. 4,876,722, issued to Dekker et al. on Oct. 24, 1989.

Road noise generated within an automobile cabin is commonly characterized by a number of low frequency resonant modes. This low frequency road noise is a problem because it is detrimental to occupant comfort and well being and because the sound absorbing material within the cabin does not significantly attenuate the low frequency noise. Generally, the conventional techniques referenced above have been successful in certain respects. However, none of the disclosed systems have achieved universal acceptance in the area of low frequency acoustic damping within an enclosure. Further, some of the systems have significant shortcomings. For example, the active noise cancellation system taught in U.S. Pat. No. 5,394,478 occupies a significant amount of space within the automobile and the active noise control system taught in U.S. Pat. No. 5,343,713, is related to control of noise in limited local areas within a three-dimensional space.

Accordingly, there is a need for a system and method that effectively reduces the amplitude of low frequency noise within an enclosure, particularly the enclosure of an automobile where the noise generated within the cabin is characterized by a number of low frequency acoustic modes of significant magnitude.

BRIEF SUMMARY OF THE INVENTION

This need is met by the present invention wherein a system for actively damping noise is provided comprising an acoustic wave sensor, and acoustic wave actuator, and an electronic feedback loop. The acoustic wave actuator is substantially collocated with the acoustic wave sensor within an enclosure. The electronic feedback loop is operative to generate a signal at its output by applying the sensed acoustic pressure to a feedback loop transfer function. The feedback loop transfer function comprises a second order differential equation including a first variable representing a predetermined damping coefficient and a second variable representing a tuned natural frequency.

In accordance with one embodiment of the present invention, a system for actively damping noise is provided comprising an enclosure, an acoustic wave sensor, and acoustic wave actuator, and an electronic feedback loop. The enclosure defines a plurality of acoustic modes. The acoustic wave sensor is positioned within the enclosure and is operative to produce a first signal representative of the plurality of acoustic modes. The acoustic wave actuator is responsive to a second signal and is positioned within the enclosure. The acoustic wave actuator is substantially collocated with the acoustic wave sensor. The electronic feedback loop defines an input coupled to the first signal and an output. The electronic feedback loop is operative to generate the second signal at the output by applying a feedback loop transfer function to the first signal. The feedback loop transfer function comprises a second order differential equation including a first variable representing a predetermined damping coefficient and a second variable representing a tuned natural frequency. Further, the feedback loop transfer function defines a frequency response having a characteristic maximum gain substantially corresponding to the value of the tuned natural frequency. Finally, the feedback loop transfer function creates a 90 degree phase lead substantially at the tuned natural frequency. The first signal represents pressure sensed by the acoustic wave sensor and the second signal represents a rate of change of volume velocity to be produced by the acoustic wave actuator.

The feedback loop transfer function may be of the following form:

$$\frac{V(s)}{P(s)} = -C\frac{\omega_n^2}{s^2 + 2\zeta\omega_n s + \omega_n^2}$$

where V(s) corresponds to the rate of change of volume velocity, P(s) corresponds to the pressure at the location of the actuator and the sensor, s is a Laplace variable, $\zeta$ is a damping coefficient, $\omega_n$ is the tuned natural frequency, and C is a constant representing either or both of a power amplification factor and a gain value. Alternatively, the feedback loop transfer function may be of the following form:

$$\frac{V(s)}{P(s)} = C\frac{s^2}{s^2 + 2\zeta\omega_n s + \omega_n^2}$$

where the units of V(s) corresponds to the rate of change of volume velocity, P(s) corresponds to the pressure at the location of the actuator and the sensor, s is a Laplace variable, $\zeta$ is a damping coefficient, $\omega$ is the tuned natural frequency, and C is a constant representing either or both of a power amplification factor and a gain value. Preferably, the feedback loop transfer function defines a frequency response wherein the gain of the frequency response increases substantially uniformly from a minimum frequency value to an intermediate frequency value to define a characteristic maximum gain and decreases substantially uniformly from the intermediate frequency value to a maximum frequency value. The intermediate frequency value preferably corresponds to the tuned natural frequency.

The first variable represents the predetermined damping coefficient and is a value between about 0.2 and about 0.5 or, more preferably, a value between about 0.3 and about 0.4. The first variable, representing the predetermined damping coefficient, and the second variable, representing the tuned natural frequency, are preferably selected to damp at least one of the plurality of acoustic modes. The second variable, representing the tuned natural frequency, is preferably selected to substantially match a target frequency of the plurality of acoustic modes, typically the lowest frequency mode, and may be offset from the target frequency of the plurality of acoustic modes so as to damp a cluster of the plurality of acoustic modes.

The electronic feedback loop is preferably further operative to invert the phase of the second signal. Further, where the acoustic wave actuator introduces an actuator phase delay into the system, the feedback loop is preferably operative to introduce a phase delay that is equal to and opposes the actuator phase delay.

In accordance with another embodiment of the present invention, a method for actively damping boom noise within an enclosure defining a plurality of acoustic modes is provided comprising the steps of: positioning an acoustic wave sensor within the enclosure, wherein the acoustic wave sensor is operative to produce a first signal representative of the plurality of acoustic modes; positioning an acoustic wave actuator responsive to a second signal within the enclosure, wherein the acoustic wave actuator is substantially collocated with the acoustic wave sensor; and, coupling an input of an electronic feedback loop to the first signal, wherein the electronic feedback loop is operative to generate the second signal at a feedback loop output by applying a feedback loop transfer function to the first signal. The feedback loop transfer function comprises a second order differential equation including a first variable representing a predetermined damping coefficient and a second variable representing a tuned natural frequency. Further, the feedback loop transfer function defines a frequency response having a characteristic maximum gain substantially corresponding to the value of the tuned natural frequency. Finally, the feedback loop transfer function creates a 90 degree phase lead substantially at the tuned natural frequency.

The method further comprises the steps of selecting a value for the first variable representing the predetermined damping coefficient, selecting a value for the second variable representing the tuned natural frequency, and operating the acoustic wave actuator in response to the second signal. The value for the first variable and the value for the second variable are preferably selected to damp at least one of the plurality of acoustic modes. For example, the value for the first variable is selected to be a value between about 0.3 and about 0.4, and the value for the second variable is selected to correspond to the lowest frequency mode of the plurality of acoustic modes.

In accordance with yet another embodiment of the present invention, a system for actively damping boom noise is provided comprising an enclosure, an acoustic wave sensor, an acoustic wave actuator, and an electronic feedback loop. The enclosure defines a plurality of acoustic modes. The acoustic wave sensor is positioned within the enclosure and is operative to produce a first signal representative of the plurality of acoustic modes. The first signal represents pressure sensed by the acoustic wave sensor. The acoustic wave actuator is responsive to a second signal, is positioned within the enclosure, is substantially collocated with the acoustic wave sensor, and introduces an actuator phase delay into the system. The second signal represents a rate of change of volume velocity to be produced by the acoustic wave actuator.

The electronic feedback loop defines an input coupled to the first signal and an output and is operative to (i) generate the second signal at the output by applying a feedback loop transfer function to the first signal, (ii) invert the phase of the second signal, and to (iii) introduce an inverted actuator phase delay into the second signal. The feedback loop transfer function comprises a second order differential equation including a first variable representing a predetermined damping coefficient and a second variable representing a tuned natural frequency. The feedback loop transfer function defines a frequency response having a characteristic maximum gain substantially corresponding to the value of the tuned natural frequency, creates a 90 degree phase lead substantially at the tuned natural frequency, and defines a frequency response having a gain that increases substantially uniformly from a minimum frequency value to an intermediate frequency value to define a characteristic maximum gain and decreases substantially uniformly from the intermediate frequency value to a maximum frequency value. The intermediate frequency value corresponds to the tuned natural frequency.

Accordingly, it is an object of the present invention to provide a system and method that effectively reduces the amplitude of low frequency noise within an enclosure, particularly the enclosure of an automobile where the noise generated within the cabin is characterized by a number of low frequency acoustic modes of significant magnitude. Other objects of the present invention will be apparent in light of the description of the invention embodied herein.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which.

DETAILED DESCRIPTION OF THE PREFERRED EMBODIMENTS

Figure 1:
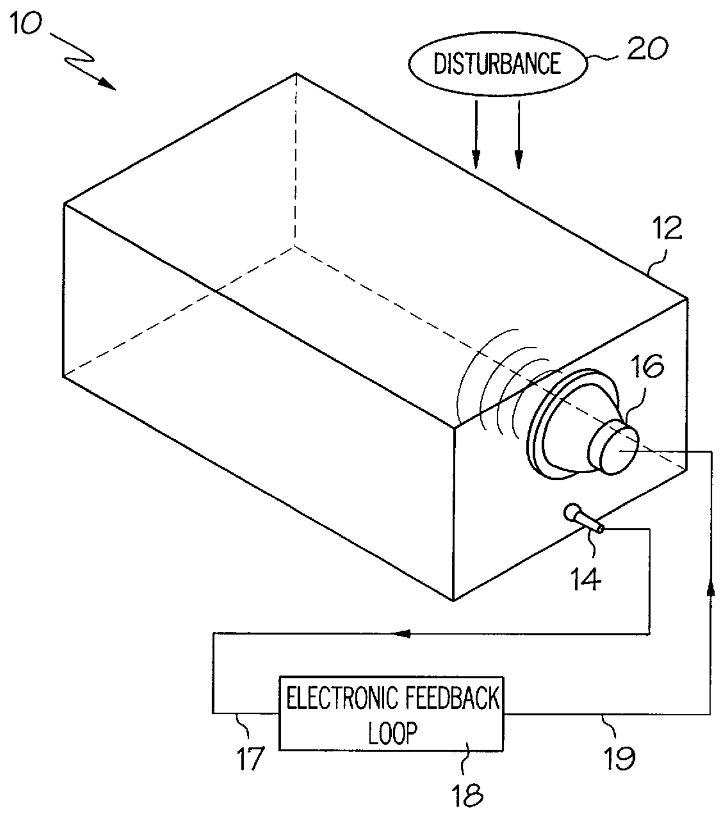
FIG. 1 is a general schematic illustration of a system for actively damping boom noise according to the present invention.

Referring initially to FIG. 1, a system for actively damping boom noise 10 according to the present invention is illustrated in general schematic form. The system 10 comprises an enclosure 12, an acoustic wave sensor 14, an acoustic wave actuator 16, and an electronic feedback loop 18. As will be appreciated by those skilled in the art of acoustics, the enclosure 12 defines a plurality of acoustic modes. The characteristics of these modes may be calculated using conventional enclosed sound propagation modeling or may be determined experimentally by positioning an enclosure of interest in an anechoic chamber, subjecting the chamber to an acoustic disturbance 20, and measuring the acoustic modes of the noise generated in the enclosure 12. The dashed lines in FIGS. 5–8 and 11–14, described in more detail below, illustrate the first three acoustic modes $m_1$, $m_2$, and $m_3$ at four different points within an enclosure 12 similar to that illustrated in FIG. 1. For the purposes of defining and describing the present invention, it should be understood that an enclosure typically comprises any completely bounded three dimensional space, but may also comprise a three dimensional space including some relatively insubstantial unbounded portions.

Figure 2:
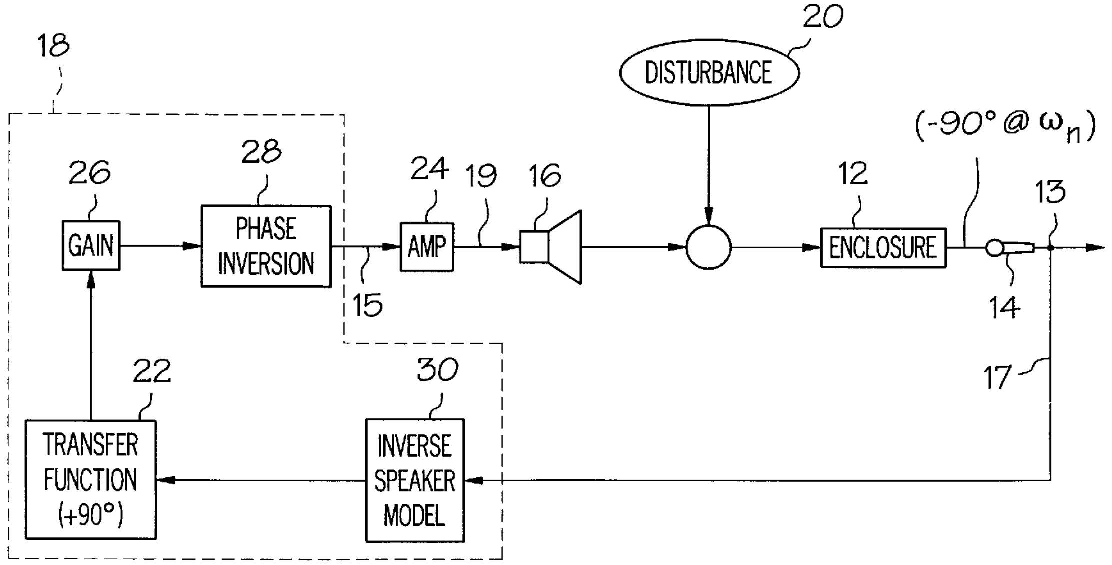
FIG. 2 is a detailed schematic block diagram of a system for actively damping boom noise according to the present invention.

The acoustic wave sensor 14 is positioned within the enclosure 12 and is operative to produce a first signal 13 representative of the plurality of acoustic modes within the enclosure 12, see FIG. 2. Specifically, the acoustic wave sensor 14 is a microphone that produces an electrical signal indicative of the pressure of the sound waves generated in the enclosure 12. The acoustic wave actuator 16 is also positioned within the enclosure 12 and is responsive to a driving signal, hereafter referred to as a second signal 15, see FIG. 2. Specifically, the second signal 15 represents a rate of change of volume velocity to be produced by the acoustic wave actuator 16. The acoustic wave actuator 16 is preferably substantially collocated with the acoustic wave sensor 14 to optimize noise damping according to the present invention. For the purposes of defining and describing the present invention, it should be understood that a substantially collocated arrangement includes any arrangement where the acoustic wave actuator 16 and the acoustic wave sensor 14 are positioned close enough to each other to ensure that the phase of the noise propagating through the enclosure 12 in the vicinity of the acoustic actuator 16 opposes the phase of the sound generated by the acoustic actuator 16 at the natural frequency of the target acoustic mode within the enclosure 12, as described in further detail below. For example, the acoustic wave actuator 16 and the acoustic wave sensor 14 are substantially collocated relative to each other when they are positioned directly adjacent to each other, as is illustrated in FIG. 1. The general position of the collocated sensor 14 and actuator 16 within the enclosure 12 may be as indicated in FIG. 1 but is preferably selected to correspond to the location of an acoustic anti-node of a target mode within the enclosure 12. The location of the anti-node may be determined by measuring pressure at a target frequency at various locations within the enclosure or through construction of an acoustic model of the enclosure.

Referring now to FIGS. 1 and 2, the electronic feedback loop 18 defines a feedback input 17 coupled to the first signal 13 and a feedback output 19. The feedback loop 18 is operative to generate the second signal 15 at the output 19 by applying a feedback loop transfer function 22 to the first signal 13. The feedback loop transfer function 22 according to the present invention comprises a second order differential equation including a first variable $\zeta$ representing a predetermined damping coefficient and a second variable representing a tuned natural frequency $\omega_n$. Two specific examples of transfer functions according to the present invention are presented in detail below with reference to equations (1) and (2). The electronic feedback loop 18 may comprise a controller programmed to apply the feedback loop transfer function 22, and the other functions associated with the feedback loop 18 described herein. Alternatively, the feedback loop 18 may comprise conventional solid state electronic devices operative to apply the functions associated with the feedback loop 18.

The first variable $\zeta$ and the second variable $\omega_n$ are selected to damp at least one of the plurality of acoustic modes $m_1$, $m_2$, and $m_3$, etc. Specifically, the first variable $\zeta$ representing the predetermined damping coefficient is a value between about 0.2 and about 0.5 or, more preferably, a value between about 0.3 and about 0.4. The second variable $\omega_n$ representing the tuned natural frequency is selected to be substantially equivalent to a natural frequency of a target acoustic mode of the plurality of acoustic modes. Typically, the target acoustic mode comprises the lowest frequency mode $m_1$ of the plurality of acoustic modes. It is contemplated by the present invention that, the second variable $\omega_n$ representing the tuned natural frequency may be selected to be offset from the target acoustic mode so as to be positioned between the characteristic frequencies of two adjacent modes. In this manner, the magnitude of a plurality of adjacent acoustic modes, e.g., $m_1$, $m_2$, may be damped.

Figure 3:
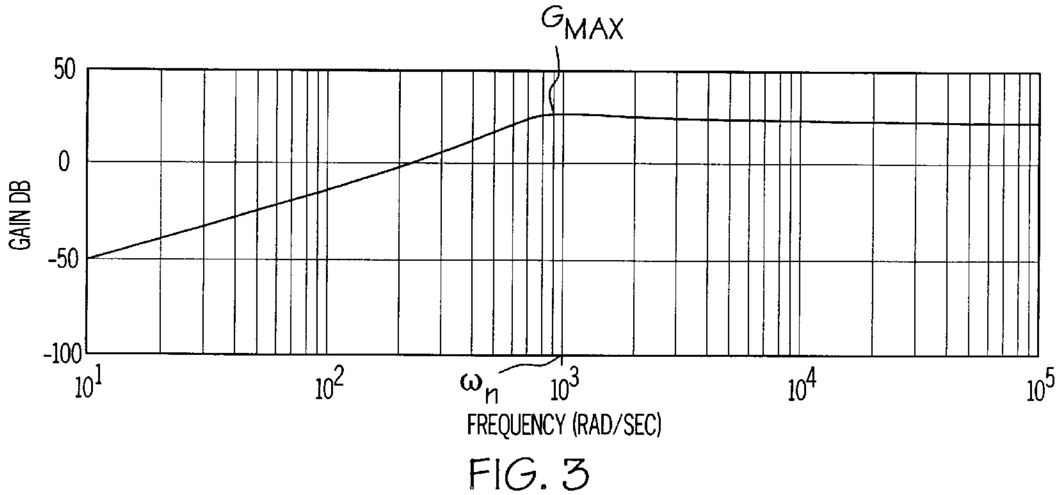
FIGS. 3 and 4 depict the frequency response of a feedback loop transfer function according to one embodiment of the present invention.
Figure 4:
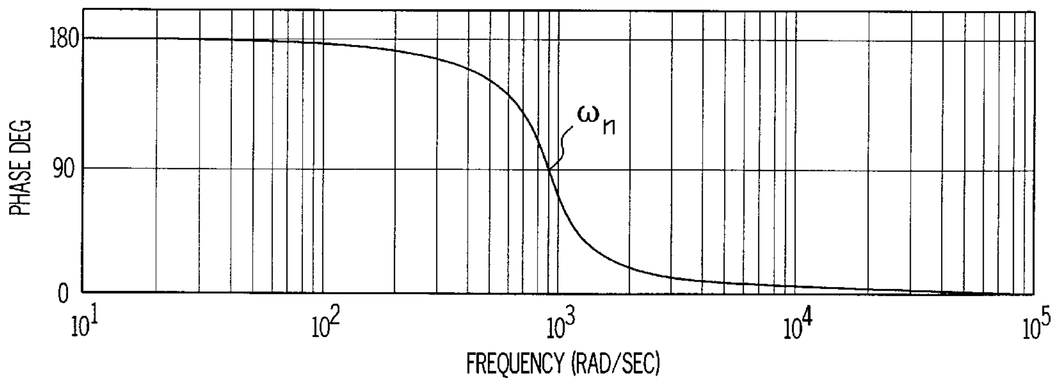
Figure 5:
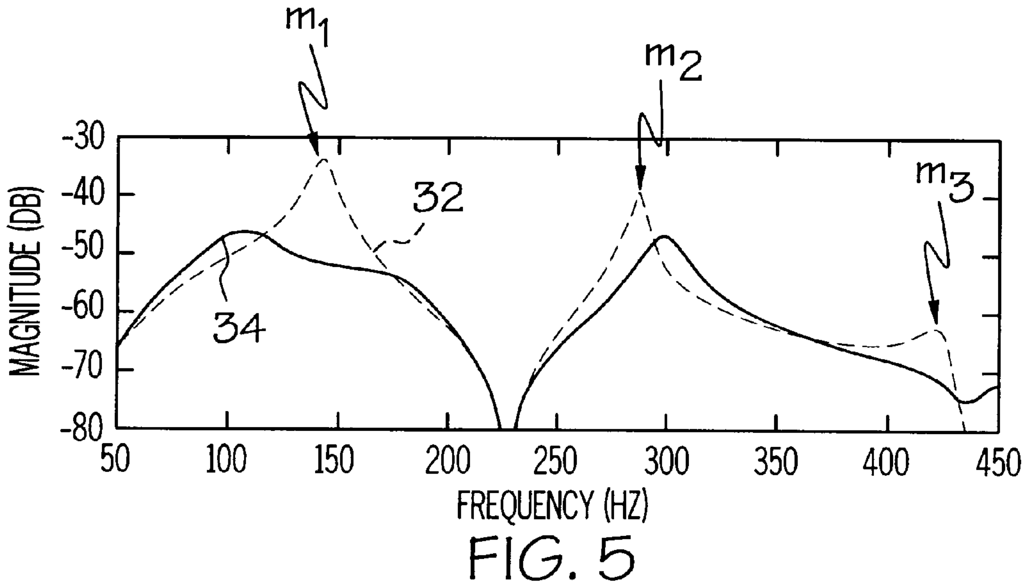
FIGS. 5–8 illustrate the acoustic damping achieved utilizing the transfer function of FIGS. 3 and 4 in a feedback loop of the present invention.
Figure 6:
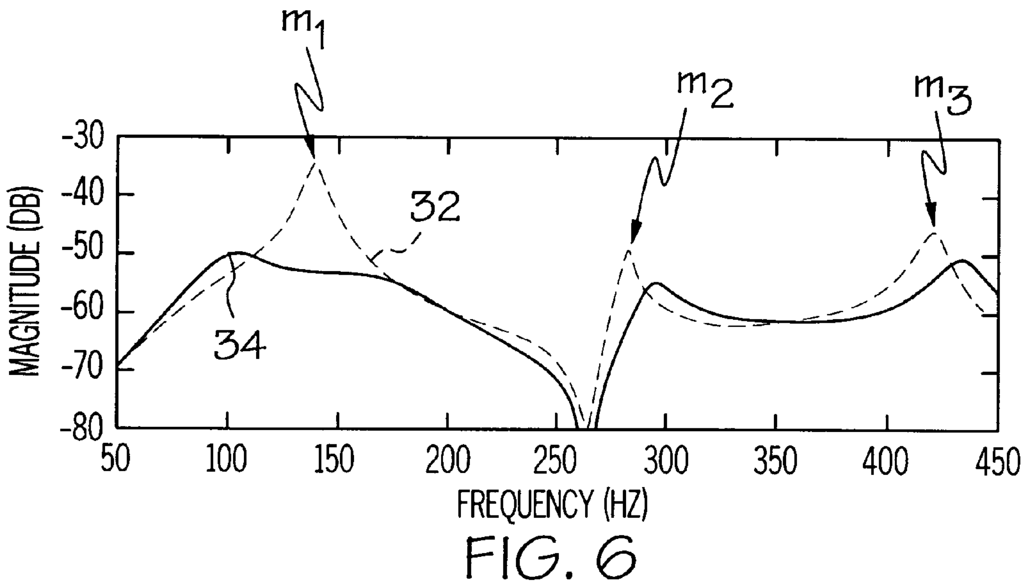
Figure 7:
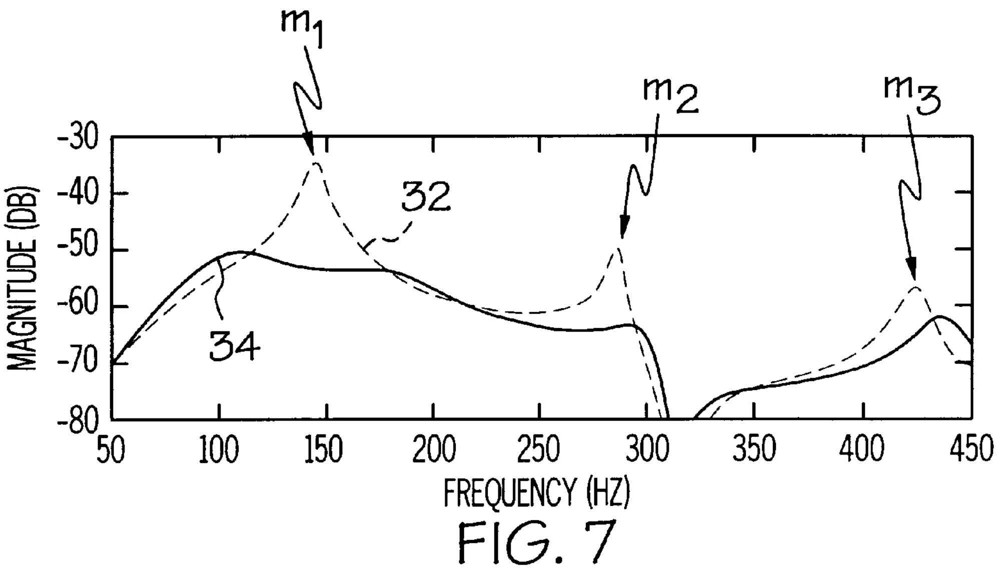
Figure 8:
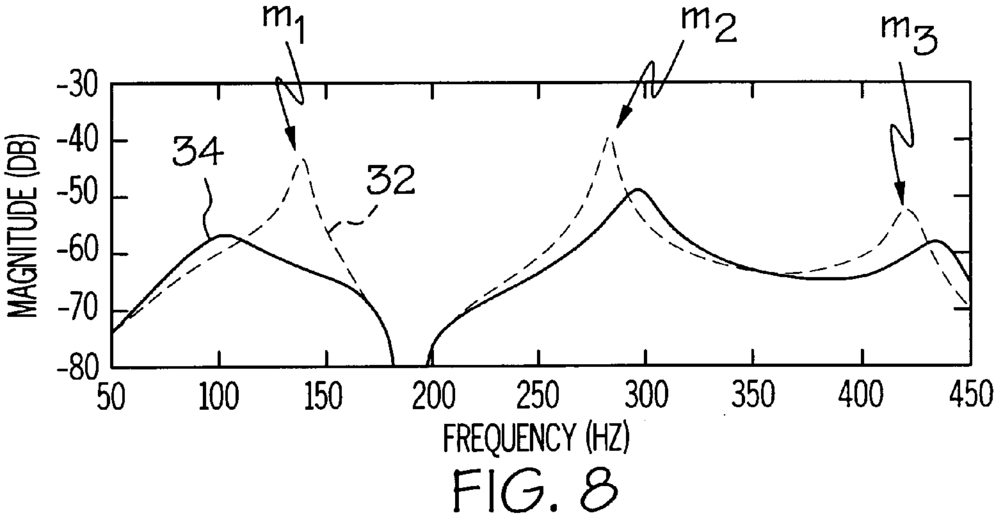

The frequency response of a first transfer function 22 according to the present invention is illustrated in FIGS. 3 and 4. The feedback loop transfer function of FIGS. 3 and 4 is as follows:

$$\frac{V(s)}{P(s)} = C\frac{s^2}{s^2 + 2\zeta\omega_n s + \omega_n^2} \tag{1}$$

where the units of V(s) corresponds to the rate of change of volume velocity, P(s) corresponds to the pressure at the location of the actuator and the sensor, s is the Laplace variable, $\zeta$ is a damping coefficient, $\omega_n$ is the tuned natural frequency, and C is a constant representing a power amplification factor and a gain value. The transfer function of equation (1) is derived from a model of a Helmholtz resonator attached to the enclosure 12 and maps the pressure in the enclosure where the actuator 16 and sensor 14 are collocated to the rate of change of volume velocity generated by the acoustic actuator 16.

Figure 9:
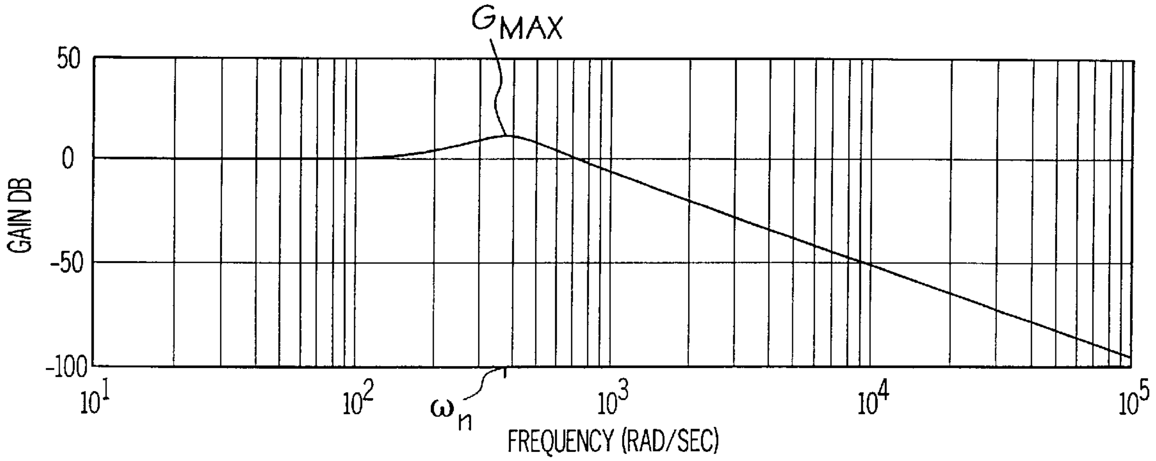
FIGS. 9 and 10 depict the frequency response of a feedback loop transfer function according to another embodiment of the present invention.
Figure 10:
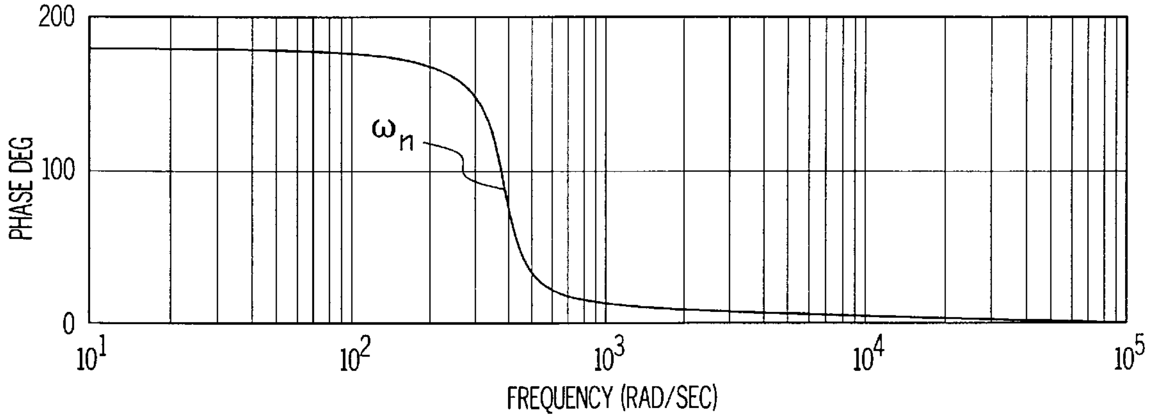
Figure 11:
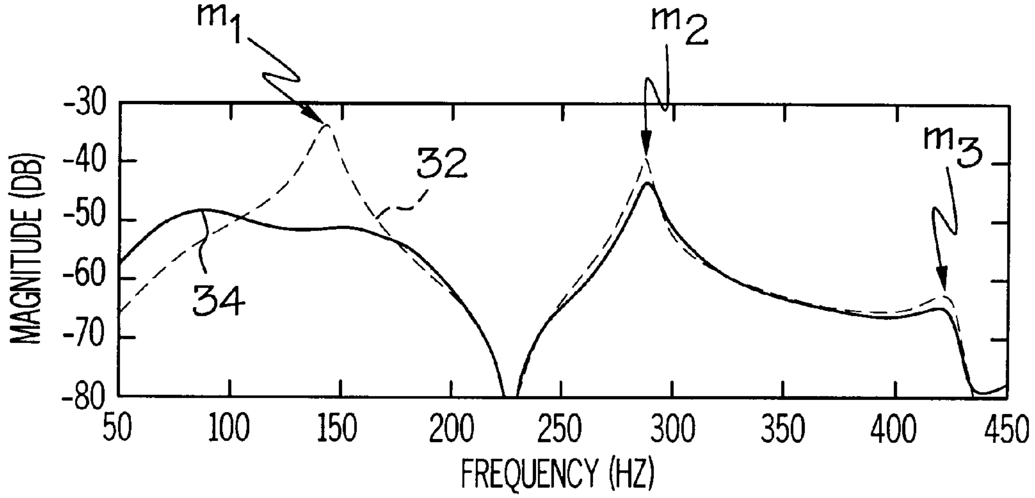
FIGS. 11–14 illustrate the acoustic damping achieved utilizing the transfer function of FIGS. 9 and 10 in a feedback loop of the present invention.
Figure 12:
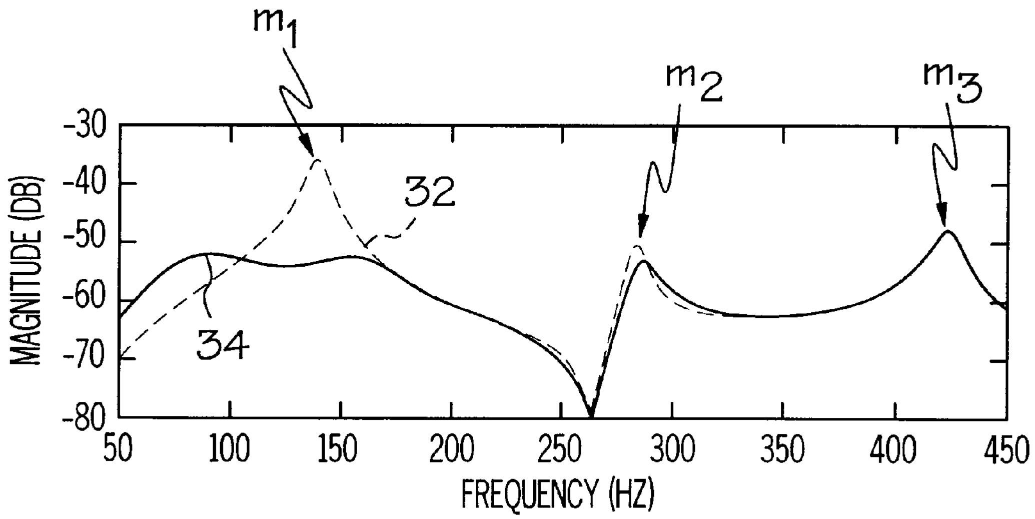
Figure 13:
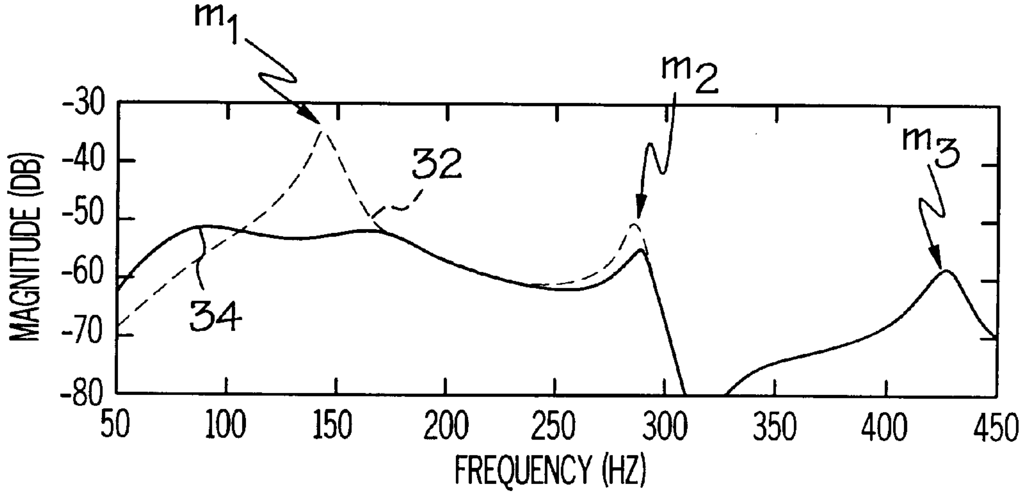
Figure 14:
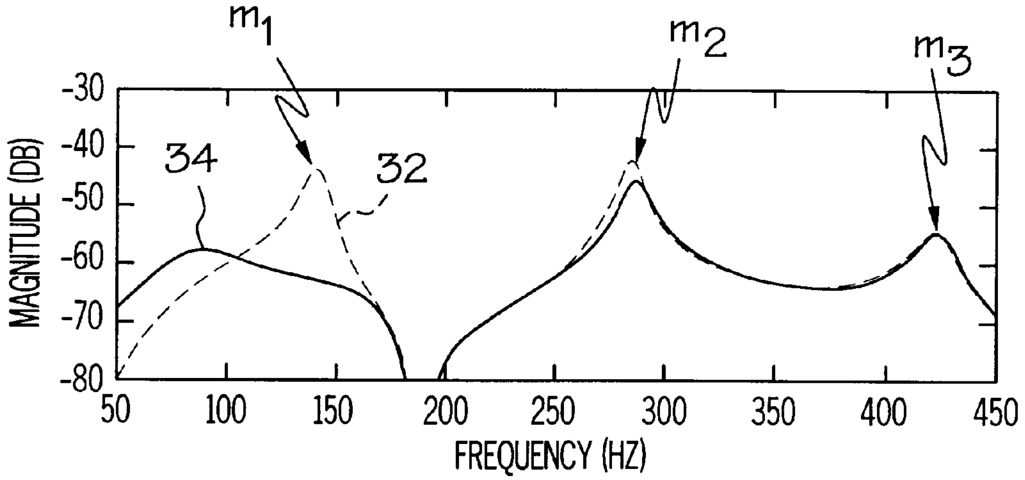

Alternatively, the frequency response of a second transfer function according to the present invention is illustrated in FIGS. 9 and 10. The feedback loop transfer function of FIGS. 9 and 10 is as follows:

$$\frac{V(s)}{P(s)} = -C\frac{\omega_n^2}{s^2 + 2\zeta\omega_n s + \omega_n^2} \tag{2}$$

where the units of V(s) corresponds to the rate of change of volume velocity, P(s) corresponds to the pressure at the location of the actuator and the sensor, s is the Laplace variable, $\zeta$ is a damping coefficient, $\omega_n$ is the tuned natural frequency, and C is a constant representing the power amplification factor and the gain value. The transfer function of equation (2) is derived from the positive position feedback active damping mechanism utilized for structural damping. It is noted that the power amplification factor 24 and the gain value 26, see FIG. 2, are dependent upon the particular specifications of the enclosure geometry, the acoustic wave sensor 14 and the acoustic wave actuator 16, and upon the amplitude of the noise created by the acoustic disturbance 20, and are subject to selection and optimization by those practicing the present invention.

Referring specifically to FIGS. 3 and 9, each illustrated feedback loop transfer function defines a frequency response having a characteristic maximum gain $G_{MAX}$ substantially corresponding to the value of the tuned natural frequency $\omega_n$. For example, with respect to the transfer functions depicted in FIGS. 3 and 9, the respective characteristic maximum gains $G_{MAX}$ and corresponding tuned natural frequency $\omega_n$ are illustrated. The gain increases substantially uniformly from a minimum frequency value to an intermediate frequency value to define the characteristic maximum gain $G_{MAX}$ and decreases from the maximum gain $G_{MAX}$ substantially uniformly from the intermediate frequency value to a maximum frequency value. For the purposes of describing and defining the present invention it is noted that a substantially uniform increase comprises an increase that is not interrupted by any temporary decreases. Similarly, a substantially uniform decrease comprises a decrease that is not interrupted by any temporary increases. A substantially uniform increase or decrease may be characterized by changes in the rate of increase or decrease.

Referring now to FIGS. 4 and 10, to further optimize low frequency noise damping according to the present invention, the respective feedback loop transfer functions depicted in FIGS. 3 and 9, create +90° phase shifts substantially at the tuned natural frequency $\omega_n$. This 90° phase lead is indicated in the transfer function block 22 of FIG. 2 and counters a 90° phase lag of the enclosure 12 at a frequency corresponding to the tuned natural frequency $\omega_n$.

A phase inversion 28 is introduced in the feedback loop 18 to invert the phase of the transfer function output signal 23 and ensure that the control action generated by the acoustic actuator 16 opposes the phase of the acoustic disturbance 20 in the enclosure 12 at the target frequency. As will be appreciated by those practicing the present invention, acoustic damping will be optimized where the acoustic wave from the actuator 16 is 180° out of phase with the acoustic disturbance at the tuned natural frequency $\omega_n$.

An inverse speaker model 30 is utilized in the feedback loop 18 to compensate for the acoustic dynamics introduced into the system by the acoustic wave actuator 16. As part of this compensation, the inverse speaker model 30 is operative to introduce a phase delay that is equal to, but opposite in sign, with respect to the phase delay introduced by the acoustic wave actuator 16.

Referring now to FIGS. 5–8, the simulated acoustic damping introduced by the transfer function of equation (1), and FIGS. 3 and 4, is illustrated. The magnitude-vs-frequency plots of FIGS. 5–8 represent damping at four different locations within the enclosure 12. Each dashed line 32 represents the magnitude of the acoustic disturbance 20 at respective points within the enclosure 12 with the feedback loop 18 open, or not operative. Each solid line 34 represents the magnitude of the damped acoustic disturbance 20 at substantially the same respective points within the enclosure 12 with the feedback loop 18 closed, or operative. To optimize damping, the respective values for $\zeta$, $\omega_n$, and the gain were set as follows: $\zeta=0.35$, $\omega_n=141$ Hz, and gain=25. Significant damping is illustrated in each of the first three acoustic modes $m_1$, $m_2$, and $m_3$.

Referring now to FIGS. 11–14, the simulated acoustic damping introduced by the transfer function of equation (2), and FIGS. 9 and 10, is illustrated. The magnitude-vs-frequency plots of FIGS. 11–14 represent damping at four different locations within the enclosure 12. Each dashed line 32 represents the magnitude of the acoustic disturbance 20 at respective points within the enclosure 12 with the feedback loop 18 open, or not operative. Each solid line 34 represents the magnitude of the damped acoustic disturbance 20 at substantially the same respective points within the enclosure 12 with the feedback loop 18 closed, or operative. To optimize damping, the respective values for $\zeta$, $\omega_n$, and the gain were selected as follows: $\zeta=0.5$, $\omega_n=141$ Hz, and gain =25. Significant damping is illustrated in each of the first three acoustic modes $m_1$, $m_2$, and $m_3$.

Referring collectively to FIGS. 5–8 and 11–14, it is noted that a significantly lower degree of low frequency softening is illustrated in the results of FIGS. 5–8. Specifically, referring to FIGS. 5–8, the magnitude of the damped acoustic disturbance 34 at frequencies below 100 Hz is only slightly higher than the magnitude of the acoustic disturbance 32 at those same frequencies while, referring to FIGS. 11–14, the magnitude of the damped acoustic disturbance 34 at frequencies below 100 Hz is more noticeably higher than the magnitude of the acoustic disturbance 32 at those same frequencies. As a note of clarification, the units of frequency utilized in FIGS. 3–14 differ between rad/sec and Hz, depending upon the particular illustration.

Accordingly, low frequency noise within the enclosure 12 is significantly damped, according to the present invention, by positioning the acoustic wave sensor 14 within the enclosure 12, positioning the acoustic wave actuator 16 within the enclosure, substantially collocating the acoustic wave sensor 14 with the acoustic wave actuator 16, and coupling the input 17 of the electronic feedback loop 18 to the signal generated by the acoustic wave sensor 14. The feedback loop 18 applies a feedback loop transfer function 22 to the input signal and generates an output signal which is coupled to the acoustic wave actuator 16. The feedback loop transfer function 22 comprises a second order differential equation including the first variable $\zeta$ representing a predetermined damping coefficient and the second variable $\omega_n$ representing a tuned natural frequency. Values for the first variable $\zeta$ and the second variable $\omega_n$ are selected to optimize damping of the low frequency mode.

Having described the invention in detail and by reference to preferred embodiments thereof, it will be apparent that modifications and variations are possible without departing from the scope of the invention defined in the appended claims.

What is claimed is:

1. A system for actively damping noise comprising:

an enclosure defining a plurality of acoustic modes;

an acoustic wave sensor positioned within said enclosure, wherein said acoustic wave sensor is operative to produce a first signal representative of said plurality of acoustic modes;

an acoustic wave actuator responsive to a second signal and positioned within said enclosure, wherein said acoustic wave actuator is substantially collocated with said acoustic wave sensor; and an electronic feedback loop defining an input coupled to said first signal and an output, wherein said electronic feedback loop is operative to generate said second signal at said output by applying a feedback loop transfer function to said first signal, and wherein said feedback loop transfer function comprises a second order differential equation including a first variable representing a predetermined damping coefficient and a second variable representing a tuned natural frequency, said second variable representing said tuned natural frequency is selected to be tuned to a natural frequency of at least one acoustic mode of said plurality of acoustic modes said feedback loop transfer function defines a frequency response having a characteristic maximum gain substantially corresponding to the value of said tuned natural frequency, and wherein said feedback loop transfer function creates a 90 degree phase lead substantially at said tuned natural frequency.

2. A system for actively damping noise as claimed in claim 1 wherein said first signal represents pressure sensed by said acoustic wave sensor and said second signal represents a rate of change of volume velocity to be produced by said acoustic wave actuator.

3. A system for actively damping noise as claimed in claim 1 wherein said first signal represents pressure sensed by said acoustic wave sensor, said second signal represents a rate of change of volume velocity to be produced by said acoustic wave actuator, and wherein said feedback loop transfer function is as follows:

$$\frac{V(s)}{P(s)} = -C\frac{\omega_n^2}{s^2 + 2\zeta\omega_n s + \omega_n^2}$$

where the units of V(s) corresponds to said rate of change of volume velocity, P(s) corresponds to the pressure at the location of the actuator and the sensor, s is a Laplace variable, $\zeta$ is a damping coefficient, $\omega_n$ is said tuned natural frequency, and C is a constant representing at least one of a power amplification factor and a gain value.

4. A system for actively damping noise as claimed in claim 1 wherein said first signal represents pressure sensed by said acoustic wave sensor, said second signal represents a rate of change of volume velocity to be produced by said acoustic wave actuator, and wherein said feedback loop transfer function is as follows:

$$\frac{V(s)}{P(s)} = C\frac{s^2}{s^2 + 2\zeta\omega_n s + \omega_n^2}$$

where the units of V(s) corresponds to said rate of change of volume velocity, P(s) corresponds to the pressure at the location of the actuator and the sensor, s is a Laplace variable, $\zeta$ is a damping coefficient, $\omega_n$ is said tuned natural frequency, and C is a constant representing at least one of a power amplification factor and a gain value.

5. A system for actively damping noise as claimed in claim 1 wherein said feedback loop transfer function defines a frequency response and wherein the gain of said frequency response increases substantially uniformly from a minimum frequency value to an intermediate frequency value to define a characteristic maximum gain and decreases substantially uniformly from said intermediate frequency value to a maximum frequency value.

6. A system for actively damping noise as claimed in claim 5 wherein said intermediate frequency value corresponds to said tuned natural frequency.

7. A system for actively damping noise as claimed in claim 1 wherein said first variable representing said predetermined damping coefficient is a value between about 0.2 and about 0.5.

8. A system for actively damping noise as claimed in claim 1 wherein said first variable representing said predetermined damping coefficient and said second variable representing said tuned natural frequency are selected to damp at least one of said plurality of acoustic modes.

9. A system for actively damping noise as claimed in claim 1 wherein said second variable representing said tuned natural frequency is selected to be substantially equivalent to a natural frequency of a target acoustic mode of said plurality of acoustic modes.

10. A system for actively damping noise as claimed in claim 9, wherein said target acoustic mode comprises the lowest frequency mode of said plurality of acoustic modes.

11. A system for actively damping noise as claimed in claim 1 wherein said second variable representing said tuned natural frequency is selected to be a value between adjacent frequency modes of said plurality of acoustic modes.

12. A system for actively damping noise as claimed in claim 1 wherein said electronic feedback loop is further operative to invert the phase of said second signal.

13. A system for actively damping noise as claimed in claim 1 wherein said acoustic wave actuator introduces characteristic acoustic dynamics into said system and wherein said feedback loop is operative to introduce inverse acoustic dynamics into said system.

14. A system for actively damping noise as claimed in claim 1 wherein said electronic feedback loop comprises a controller programmed to apply said feedback loop transfer function.

15. A system for actively damping noise as claimed in claim 1 wherein said first signal and said second signal comprise respective electric signals.

16. A system for actively damping noise as claimed in claim 1 wherein said acoustic wave actuator and said acoustic wave sensor are positioned to correspond to the location of an acoustic anti-node of a target acoustic mode within the enclosure.

17. A method for actively damping noise within an enclosure defining a plurality of acoustic modes comprising the steps of:

positioning an acoustic wave sensor within said enclosure, wherein said acoustic wave sensor is operative to produce a first signal representative of said plurality of acoustic modes;

positioning an acoustic wave actuator responsive to a second signal within said enclosure, wherein said acoustic wave actuator is substantially collocated with said acoustic wave sensor;

coupling an input of an electronic feedback loop to said first signal, wherein said electronic feedback loop is operative to generate said second signal at a feedback loop output by applying a feedback loop transfer function to said first signal, and wherein said feedback loop transfer function comprises a second order differential equation including a first variable representing a predetermined damping coefficient and a second variable representing a tuned natural frequency, said second variable representing said tuned natural frequency is selected to be tuned to a natural frequency of at least one acoustic mode of said plurality of acoustic modes said feedback loop transfer function defines a frequency response having a characteristic maximum gain substantially corresponding to the value of said tuned natural frequency, and wherein said feedback loop transfer function creates a 90 degree phase lead substantially at said tuned natural frequency;

selecting a value for said first variable representing said predetermined damping coefficient;

selecting a value for said second variable representing said tuned natural frequency; and operating said acoustic wave actuator in response to said second signal.

18. A method for actively damping noise within an enclosure as claimed in claim 17 wherein said value for said first variable and said value for said second variable are selected to damp at least one of said plurality of acoustic modes.

19. A method for actively damping noise within an enclosure as claimed in claim 17 wherein said value for said first variable is selected to be a value between about 0.3 and about 0.4, and wherein said value for said second variable is selected to correspond to the lowest frequency mode of said plurality of acoustic modes.

20. A system for actively damping noise comprising:

an enclosure defining a plurality of acoustic modes;

an acoustic wave sensor positioned within said enclosure, wherein said acoustic wave sensor is operative to produce a first signal representative of said plurality of acoustic modes, and wherein said first signal represents pressure sensed by said acoustic wave sensor;

an acoustic wave actuator responsive to a second signal and positioned within said enclosure, wherein said acoustic wave actuator is substantially collocated with said acoustic wave sensor, wherein said second signal represents a rate of change of volume velocity to be produced by said acoustic wave actuator, and wherein said acoustic wave actuator introduces acoustic dynamics into said system; and an electronic feedback loop defining an input coupled to said first signal and an output, wherein said electronic feedback loop is operative to generate said second signal at said output by applying a feedback loop transfer function to said first signal, invert the phase of said second signal, and to introduce inverted actuator acoustic dynamics into said second signal, and wherein said feedback loop transfer function comprises a second order differential equation including a first variable representing a predetermined damping coefficient and a second variable representing a tuned natural frequency, wherein said second variable representing said tuned natural frequency is selected to be tuned to a natural frequency of at least one acoustic mode of said plurality of acoustic modes, and wherein said transfer function is selected from the group consisting of $$\frac{V(s)}{P(s)} = -C\frac{\omega_n^2}{s^2 + 2\zeta\omega_n s + \omega_n^2}$$

and $$\frac{V(s)}{P(s)} = C\frac{s^2}{s^2 + 2\zeta\omega_n s + \omega_n^2}$$

where the units of V(s) corresponds to said rate of change of volume velocity, P(s) corresponds to the pressure at the location of the actuator and the sensor, s is a Laplace variable, $\zeta$ is a damping coefficient, $\omega_n$ is said tuned natural frequency, and C is a constant representing at least one of a power amplification factor and a gain value, said feedback loop transfer function defines a frequency response having a characteristic maximum gain substantially corresponding to the value of said tuned natural frequency, said feedback loop transfer function creates a 90 degree phase lead substantially at said tuned natural frequency, said feedback loop transfer function defines a frequency response having a gain that increases substantially uniformly from a minimum frequency value to an intermediate frequency value to define a characteristic maximum gain and decreases substantially uniformly from said intermediate frequency value to a maximum frequency value, and wherein said intermediate frequency value corresponds to said tuned natural frequency.

* * * * *

UNITED STATES PATENT AND TRADEMARK OFFICE

CERTIFICATE OF CORRECTION

PATENT NO. : 5,974,155
DATED : October 26, 1999
INVENTOR(S) : Ahmad Reza Kashani It is certified that error appears in the above-identified patent and that said Letters Patent is hereby corrected as shown below:

Title page,
Item [75], Inventors, the first named inventor should read as -- Ahmad Reza Kashani --.

Signed and Sealed this

Twentieth Day of August, 2002

*Attest:*

JAMES E. ROGAN

*Attesting Officer* *Director of the United States Patent and Trademark Office*

UNITED STATES PATENT AND TRADEMARK OFFICE

CERTIFICATE OF CORRECTION

PATENT NO. : 5,974,155
DATED : October 26, 1999
INVENTOR(S) : Ahmad Reza Kashani and David Naastad It is certified that error appears in the above-identified patent and that said Letters Patent is hereby corrected as shown below:

Title page,
Item [75], Inventors: "Reza Kashani" should be -- Ahmad Reza Kashani --

Signed and Sealed this

Twenty-eighth Day of January, 2003

JAMES E. ROGAN
*Director of the United States Patent and Trademark Office*